(12) United States Patent
Sluder et al.

(10) Patent No.: US 12,064,146 B2
(45) Date of Patent: *Aug. 20, 2024

(54) ANTERIOR CERVICAL FIXATION PLATE FOR FIXATING PORTIONS OF A CERVICAL SPINE TO FACILITATE BONE FUSION

(71) Applicant: MiRus LLC, Marietta, GA (US)

(72) Inventors: Justin C. Sluder, Dallas, GA (US); Wayne Gray, Atlanta, GA (US)

(73) Assignee: MiRus LLC, Marietta, GA (US)

( * ) Notice: Subject to any disclaimer, the term of this patent is extended or adjusted under 35 U.S.C. 154(b) by 518 days.

This patent is subject to a terminal disclaimer.

(21) Appl. No.: 17/240,449

(22) Filed: Apr. 26, 2021

(65) Prior Publication Data
US 2022/0079633 A1  Mar. 17, 2022

Related U.S. Application Data

(63) Continuation of application No. 16/422,014, filed on May 24, 2019, now Pat. No. 10,987,140.

(60) Provisional application No. 62/676,649, filed on May 25, 2018.

(51) Int. Cl.
  *A61B 17/80* (2006.01)
  *A61B 17/70* (2006.01)
  *A61B 17/86* (2006.01)

(52) U.S. Cl.
  CPC ...... *A61B 17/7059* (2013.01); *A61B 17/8061* (2013.01); *A61B 17/8004* (2013.01); *A61B 17/8605* (2013.01)

(58) Field of Classification Search
  CPC ............ A61B 17/7059; A61B 17/8061; A61B 17/8004; A61B 17/8605
  USPC ....... 606/279, 280, 281, 286, 287, 289, 292, 606/295, 298, 300, 305, 319
  See application file for complete search history.

(56) References Cited

U.S. PATENT DOCUMENTS

| | | | |
|---|---|---|---|
| 6,139,550 A | 10/2000 | Michelson |
| 6,224,602 B1 | 5/2001 | Hayes |
| 6,306,136 B1 | 10/2001 | Baccelli |
| 6,602,256 B1 | 8/2003 | Hayes |
| 6,602,257 B1 | 8/2003 | Thramann |
| 6,679,883 B2 | 1/2004 | Hawkes et al. |
| 7,220,263 B2 | 5/2007 | Cordaro |
| 7,306,605 B2 | 12/2007 | Ross |

(Continued)

*Primary Examiner* — Eduardo C Robert
*Assistant Examiner* — David C Comstock
(74) *Attorney, Agent, or Firm* — UB Greensfelder LLP; Brian Erkin Turung (57) ABSTRACT

Various implementations include an anterior cervical fixation plate for fixating portions of a cervical spine to facilitate bone fusion. The plate includes a first portion, a second portion, and a bridge. A first surface of the first portion and a first surface of the second portion each define two fastener openings extending from the first surface of the first portion to a second surface of the first portion. The first side and the second side of the centrally located bridge each extend from the second side of the first portion to the first side of the second portion. The second side of the first portion, the first side of the second portion, and the first side of the bridge define a first window. The second side of the first portion, the first side of the second portion, and the second side of the bridge define a second window.

10 Claims, 5 Drawing Sheets

(56) References Cited

U.S. PATENT DOCUMENTS

| | | | |
|---|---|---|---|
| 9,039,744 B2* | 5/2015 | Goodman | A61B 17/8042 |
| | | | 606/246 |
| 9,119,682 B2* | 9/2015 | Stoll | A61B 17/809 |
| 11,229,460 B2* | 1/2022 | Wolfe | A61B 17/8605 |
| 2003/0018335 A1 | 1/2003 | Michelson | |
| 2003/0083658 A1 | 5/2003 | Hawkes | |
| 2005/0261690 A1 | 11/2005 | Binder | |
| 2009/0171396 A1* | 7/2009 | Baynham | A61B 17/863 |
| | | | 606/301 |
| 2009/0270927 A1 | 10/2009 | Perrow | |
| 2011/0106159 A1* | 5/2011 | Nazeck | A61B 17/7059 |
| | | | 606/246 |
| 2011/0184415 A1 | 7/2011 | Anderson | |
| 2013/0184765 A1 | 7/2013 | Beyar | |
| 2016/0262905 A1* | 9/2016 | Prado | A61B 17/7059 |
| 2017/0007300 A1 | 1/2017 | Garrido | |
| 2018/0303521 A1 | 10/2018 | Hynes | |
| 2019/0008995 A1 | 1/2019 | Roth | |
| 2020/0038078 A1 | 2/2020 | Pascal-Moussellard | |

* cited by examiner

ANTERIOR CERVICAL FIXATION PLATE FOR FIXATING PORTIONS OF A CERVICAL SPINE TO FACILITATE BONE FUSION

CROSS-REFERENCE TO RELATED APPLICATIONS

This application is a continuation of U.S. Ser. No. 16/422,014 filed May 24, 2019 (now U.S. Pat. No. 10,987,140), which in turn claims the benefit of U.S. provisional patent application No. 62/676,649, filed on May 25, 2018, and entitled "ANTERIOR CERVICAL FIXATION PLATE SYSTEM," the disclosure disclosures of which is are expressly incorporated herein by reference in its entirety their entireties.

BACKGROUND

Anterior cervical fixation plates are spine implants that are used to fixate portions of a cervical spine to facilitate bone fusion. The plates include fasteners (typically screws) for affixing the plate to multiple vertebral bodies, which facilitates bone fusion by stabilizing sections of the cervical spine following anterior cervical discectomy and corpectomy procedures.

Before an anterior cervical fixation plate can be affixed to the spine of a patient, the tissue surrounding the spine must be retracted to expose enough of the vertebral bodies to insert and position the plate. Further, any osteophytes formed at the bases of the vertebral bodies must be removed so that the plate can be placed flat on the vertebrae. However, excessive retraction of the tissue surrounding the spine can cause dysphagia in the patient and can lead to longer recovery times. The removal of osteophytes from the vertebrae can also lead to longer surgery time and longer recovery.

Thus, a need exists for an anterior cervical fixation plate that can be implanted with less retraction of tissue and less removal of osteophytes.

SUMMARY

Anterior cervical fixation plates for fixating portions of a cervical spine to facilitate bone fusion are described herein. An example anterior cervical fixation plate includes a first portion, a second portion, and a bridge. The first portion has a first surface, a second surface opposite and spaced apart from the first surface of the first portion, a first side, a second side opposite and spaced apart from the first side of the first portion, a third side, a fourth side opposite and spaced apart from the third side of the first portion, and a first axis extending from the third side of the first portion to the fourth side of the first portion. The first surface of the first portion defines a first fastener opening and a second fastener opening. Each of the first fastener opening and the second fastener opening are aligned along the first axis. Each of the first fastener opening and the second fastener opening extend from the first surface of the first portion to the second surface of the first portion.

The second portion has a first surface, a second surface opposite and spaced apart from the first surface of the second portion, a first side, a second side opposite and spaced apart from the first side of the second portion, a third side, a fourth side opposite and spaced apart from the third side of the second portion, and a second axis extending from the third side of the second portion to the fourth side of the second portion. The first surface of the second portion defines a third fastener opening and a fourth fastener opening. Each of the third fastener opening and the fourth fastener opening are aligned along the second axis. Each of the third fastener opening and the fourth fastener opening extend from the first surface of the second portion to the second surface of the second portion.

The bridge has a first surface, a second surface opposite and spaced apart from the first surface of the bridge, a first side, and a second side opposite and spaced apart from the first side of the bridge. The bridge is centrally located between the first portion and the second portion, and the first side and the second side of the bridge each extend from the second side of the first portion to the first side of the second portion. The second side of the first portion, the first side of the second portion, and the first side of the bridge define a first window. The second side of the first portion, the first side of the second portion, and the second side of the bridge define a second window.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF DRAWINGS

Example features and implementations are disclosed in the accompanying drawings. However, the present disclosure is not limited to the precise arrangements and instrumentalities shown. Similar elements in different implementations are designated using the same reference numerals.

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. As used herein, the terms "about" or "approximately", when used in reference to a linear dimension (e.g., width, thickness, etc.), mean within plus or minus 10 percentage of the referenced the linear dimension.

The devices and systems disclosed herein provide for anterior cervical fixation plates for fixating portions of a cervical spine to facilitate bone fusion. The plates have two or more portions and each portion of the plate defines at least two fastener openings. In other words, the plate has two points of fixation per level such that it accommodates two fasteners (e.g., screws) per vertebral body. Each set of adjacent portions of the plate are adjoined by a bridge extending between the portions. Because the plate is manufactured from a strong material such as an alternative medical grade material as described herein, the plate is designed with smaller dimensions. The smaller plate allows the plate to be affixed to the spine of a patient with less disruption of tissue, lowering the risk of surgical complications and shortening recovery times.

Various implementations include an anterior cervical fixation plate for fixating portions of a cervical spine to facilitate bone fusion. The plate includes a first portion, a second portion, and a bridge. The first portion has a first surface, a second surface opposite and spaced apart from the first surface of the first portion, a first side, a second side opposite and spaced apart from the first side of the first portion, a third side, a fourth side opposite and spaced apart from the third side of the first portion, and a first axis extending from the third side of the first portion to the fourth side of the first portion. The first surface of the first portion defines a first fastener opening and a second fastener opening. Each of the first fastener opening and the second fastener opening are aligned along the first axis. Each of the first fastener opening and the second fastener opening extend from the first surface of the first portion to the second surface of the first portion.

The second portion has a first surface, a second surface opposite and spaced apart from the first surface of the second portion, a first side, a second side opposite and spaced apart from the first side of the second portion, a third side, a fourth side opposite and spaced apart from the third side of the second portion, and a second axis extending from the third side of the second portion to the fourth side of the second portion. The first surface of the second portion defines a third fastener opening and a fourth fastener opening. Each of the third fastener opening and the fourth fastener opening are aligned along the second axis. Each of the third fastener opening and the fourth fastener opening extend from the first surface of the second portion to the second surface of the second portion.

The bridge has a first surface, a second surface opposite and spaced apart from the first surface of the bridge, a first side, and a second side opposite and spaced apart from the first side of the bridge. The bridge is centrally located between the first portion and the second portion, and the first side and the second side of the bridge each extend from the second side of the first portion to the first side of the second portion. The second side of the first portion, the first side of the second portion, and the first side of the bridge define a first window. The second side of the first portion, the first side of the second portion, and the second side of the bridge define a second window.

Various other implementations include an anterior cervical fixation plate for fixating portions of a cervical spine to facilitate bone fusion. The plate includes a first portion, a second portion, and a bridge. The first portion has a first surface, a second surface opposite and spaced apart from the first surface of the first portion, a first side, a second side opposite and spaced apart from the first side of the first portion, a third side, a fourth side opposite and spaced apart from the third side of the first portion, and a first axis extending from the third side of the first portion to the fourth side of the first portion. The first surface of the first portion defines a first fastener opening and a second fastener opening. Each of the first fastener opening and the second fastener opening are aligned along the first axis. Each of the first fastener opening and the second fastener opening extend from the first surface of the first portion to the second surface of the first portion.

The second portion has a first surface, a second surface opposite and spaced apart from the first surface of the second portion, a first side, a second side opposite and spaced apart from the first side of the second portion, a third side, a fourth side opposite and spaced apart from the third side of the second portion, and a second axis extending from the third side of the second portion to the fourth side of the second portion. The first surface of the second portion defines a third fastener opening and a fourth fastener opening. Each of the third fastener opening and the fourth fastener opening are aligned along the second axis. Each of the third fastener opening and the fourth fastener opening extend from the first surface of the second portion to the second surface of the second portion.

The bridge has a first surface, a second surface opposite and spaced apart from the first surface of the bridge, a first side, and a second side opposite and spaced apart from the first side of the bridge. The bridge is centrally located between the first portion and the second portion, and the first side and the second side of the bridge each extend from the second side of the first portion to the first side of the second portion. The plate has a maximum thickness defined as the largest of the distance from the first surface of the first portion to the second surface of the first portion, the distance from the first surface of the second portion to the second surface of the second portion, or the distance from the first surface of the bridge to the second surface of the bridge. The maximum thickness is 2 mm or less.

Various other implementations include an anterior cervical fixation plate for fixating portions of a cervical spine to facilitate bone fusion. The plate includes a first portion, a second portion, and a bridge. The first portion has a first surface, a second surface opposite and spaced apart from the first surface of the first portion, a first side, a second side opposite and spaced apart from the first side of the first portion, a third side, a fourth side opposite and spaced apart from the third side of the first portion, and a first axis extending from the third side of the first portion to the fourth side of the first portion. The first surface of the first portion defines a first fastener opening and a second fastener opening. Each of the first fastener opening and the second fastener opening are aligned along the first axis. Each of the first fastener opening and the second fastener opening extend from the first surface of the first portion to the second surface of the first portion.

The second portion has a first surface, a second surface opposite and spaced apart from the first surface of the second portion, a first side, a second side opposite and spaced apart from the first side of the second portion, a third side, a fourth side opposite and spaced apart from the third side of the second portion, and a second axis extending from the third side of the second portion to the fourth side of the second portion. The first surface of the second portion defines a third fastener opening and a fourth fastener opening. Each of the third fastener opening and the fourth fastener opening are aligned along the second axis. Each of the third fastener opening and the fourth fastener opening extend from the first surface of the second portion to the second surface of the second portion.

The bridge has a first surface, a second surface opposite and spaced apart from the first surface of the bridge, a first side, and a second side opposite and spaced apart from the first side of the bridge. The bridge is centrally located between the first portion and the second portion, and the first side and the second side of the bridge each extend from the second side of the first portion to the first side of the second portion. The bridge has a bridge width from the first side of the bridge to the second side of the bridge. The bridge width is 4.3 mm or less.

Figure 1A:
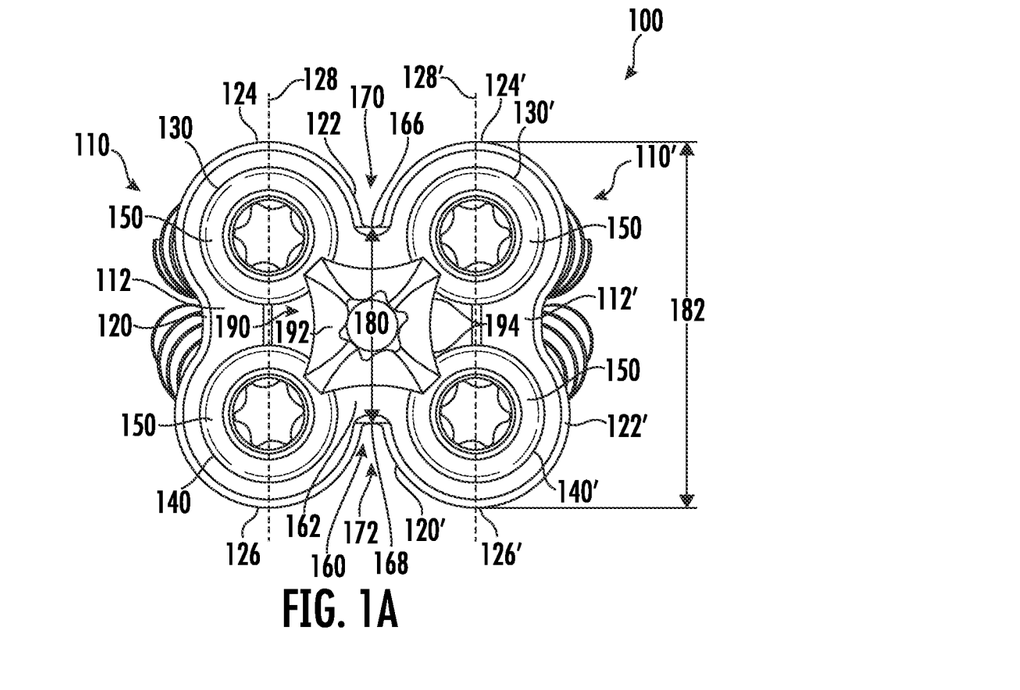
FIG. 1A is a top view of an anterior cervical fixation plate, according to one implementation.
Figure 1B:
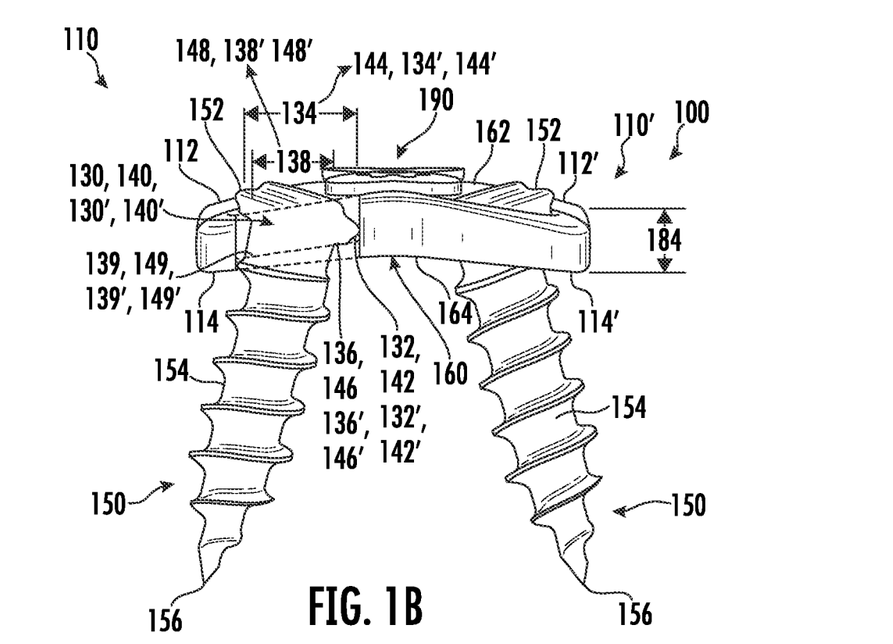
FIG. 1B is a side view of the anterior cervical fixation plate of FIG. 1A.

FIGS. 1A and 1B show a top view and a side view of an anterior cervical fixation plate 100 for fixating portions of a cervical spine to facilitate bone fusion. The plate 100 includes a first portion 110, a second portion 110', and a bridge 160. This disclosure contemplates that the first portion 110 can attach at a first level (e.g., a first vertebral body) and the second portion 110' can attach at a second level (e.g., a second vertebral body), and the bridge 160 connects the first and second portions 110, 110'. The plate 100 can accommodate four fasteners 150, e.g., two per level or two per vertebral body.

The first portion 110 of the plate 100 has a first surface 112 and a second surface 114 opposite and spaced apart from the first surface 112. The first portion 110 also has a first side 120, a second side 122 opposite and spaced apart from the first side 120 of the first portion 110, a third side 124, and a fourth side 126 opposite and spaced apart from the third side 124 of the first portion 110. The first 120, second 122, third 124, and fourth sides 126 extend between the first surface 112 and the second surface 114. The first portion 110 further includes a first axis 128 extending from the center of the third side 124 of the first portion 110 to the center of the fourth side 126 of the first portion 110.

The second portion 110' of the plate 100 has a first surface 112' and a second surface 114' opposite and spaced apart from the first surface 112'. The second portion 110' also has a first side 120', a second side 122' opposite and spaced apart from the first side 120' of the second portion 110', a third side 124', and a fourth side 126' opposite and spaced apart from the third side 124' of the second portion 110'. The first 120', second 122', third 124', and fourth sides 126' extend between the first surface 112' and the second surface 114'. The second portion 110' further includes a second axis 128' extending from the center of the third side 124' of the second portion 110' to the center of the fourth side 126' of the second portion 110'.

The bridge 160 has a first surface 162 and a second surface 164 opposite and spaced apart from the first surface 162 of the bridge 160. The bridge 160 also has a first side 166 and a second side 168 opposite and spaced apart from the first side 166 of the bridge 160. The bridge 160 is centrally located between the first portion 110 and the second portion 110', and the first side 166 and the second side 168 of the bridge 160 each extend from the second side 122 of the first portion 110 to the first side 120' of the second portion 110'. The plate 100 shown in FIGS. 1A and 1B has only one bridge 160 structure extending between the first portion 110 and the second portion 110'. As used herein, the term "bridge" is used to describe all of the structures extending between two adjacent portions. Thus, if a plate has two or more separate structures extending between two adjacent portions, then the combination of all of the structures extending between the two adjacent portions constitutes a single bridge.

The bridge 160 of the plate 100 has a bridge width 180 as measured from the first side 166 of the bridge 160 to the second side 168 of the bridge 160. The plate 100 also has a plate width 182 defined as the largest of the distance from the third side 124 of the first portion 110 to the fourth side 126 of the first portion 110 or the distance from the third side 124' of the second portion 110' to the fourth side 126' of the second portion 110'. As shown in FIGS. 1A and 1B, the bridge width 180 is less than the plate width 182. A portion of the second side 122 of the first portion 110, a portion of the first side 120' of the second portion 110', and the first side 166 of the bridge 160 define a first window 170, and a portion of the second side 122 of the first portion 110, a portion of the first side 120' of the second portion 110', and the second side 168 of the bridge 160 define a second window 172. When the plate 100 is being affixed to portions of a cervical spine 196, the windows 170, 172 allow the physician to see the intervertebral space between the two vertebrae 198. Thus, the physician can use the windows 170, 172 to determine the correct location of the plate 100 before affixing the plate 100.

The first surface 112 of the first portion 110 defines a first fastener opening 130 and a second fastener opening 140. Each of the first fastener opening 130 and the second fastener opening 140 are aligned along the first axis 128 such that first axis 128 passes through at least a portion of the fastener openings 130, 140. Each of the first fastener opening 130 and the second fastener opening 140 extend from the first surface 112 of the first portion 110 to the second surface 114 of the first portion 110. The first fastener opening 130 and the second fastener opening 140 each have a first section 132, 142 with a first diameter 134, 144 and a second section 136, 146 with a second diameter 138, 148 that is smaller than the first diameter 134, 144. The first section 132, 142 of each fastener opening 130, 140 is closer than the second section 136, 146 to the first surface 112 of the first portion 110. Because the first diameters 134, 144 are larger than the second diameters 138, 148, the intersection of the first section 132, 142 and the second section 136, 146 of each fastener opening 130, 140 forms a lip 139, 149.

The first surface 112' of the second portion 110', similarly, defines a third fastener opening 130' and a fourth fastener opening 140'. Each of the third fastener opening 130' and the fourth fastener opening 140' are aligned along the second axis 128' such that second axis 128' passes through at least a portion of the fastener openings 130', 140'. Each of the third fastener opening 130' and the fourth fastener opening 140' extend from the first surface 112' of the second portion 110' to the second surface 114' of the second portion 110'. The third fastener opening 130' and the fourth fastener opening 140' each have a first section 132', 142' with a first diameter 134', 144' and a second section 136', 146' with a second diameter 138', 148' that is smaller than the first diameter 134', 144'. The first section 132', 142' of each fastener opening 130', 140' is closer than the second section 136', 146' to the first surface 112' of the second portion 110'.

Because the first diameters 134', 144' are larger than the second diameters 138', 148', the intersection of the first section 132', 142' and the second section 136', 146' of each fastener opening 130', 140' forms a lip 139', 149'.

The first diameters 134, 144, 134', 144' of the first 130, second 140, third 130', and fourth fastener openings 140' are sized such that the head 152 of a fastener 150 is able to be disposed within the first section 132, 142, 132', 142'. The second diameters 138, 148, 138', 148' of the first 130, second 140, third 130', and fourth fastener openings 140' are large enough such that the shaft 154 of a fastener 150 is able to be disposed within the second section 136, 146, 136', 146' but are small enough such that the head 152 of the fastener 150 cannot pass through the second section 136, 146, 136', 146'. When a fastener 150 is fully inserted into a fastener opening 130, 140, 130', 140', the head 152 of the fastener 150 can abut the lip 139, 149, 139', 149' of the fastener opening 130, 140, 130', 140'.

The first portion 110, the second portion 110', and the bridge 160 of the plate 100 shown in FIGS. 1A and 1B can optionally made of a Molybdenum-Rhenium (MoRe) alloy, for example, Mo47.5Re. A MoRe alloy can be chosen as the material for the plate 100 because of its superior strength as compared to other medical grade alloys. The strength of MoRe allows for the manufacturing of an anterior cervical fixation plate 100 with smaller overall dimensions than anterior cervical fixation plate manufactured from other materials. Although the plate 100 shown in FIGS. 1A and 1B is made of Mo47.5Re, in other implementations, the plate is made of any material at least 40 weight percent Rhenium (Re). In some implementations, the plate is made of a Titanium-Molybdenum (TiMo) alloy, such as Ti45Mo. In some implementations, the plate is made of a Cobalt-Chromium (CoCr) alloy. In some implementations, the plate is made of a Titanium alloy. Additional medical grade alloys are described below.

In the plates 100 described herein, the bridge width 180 is smaller than the plate width 182. This results in definition of windows 170, 172, which allow the physician to see the intervertebral space between the two vertebrae 198. For example, the bridge width 180 of the plate 100 shown in FIGS. 1A and 1B is 4.3 mm. In other implementations, the bridge width can be between about 3.5 mm and 5.5 mm (e.g., 3.50 mm, 3.51 mm, 3.52 mm . . . 5.48 mm, 5.49 mm, 5.50 mm) and any value or range therebetween. The plate width 182 of the plate 100 shown in FIGS. 1A and 1B is 14.3 mm, but in other implementations, the plate width can be any width greater than the bridge width. This disclosure contemplates that the minimum plate width 182 is about 12 mm, which is limited by the size of the fasteners. Accordingly, the plate width 182 can be between about 12 mm and 14.3 mm (e.g., 12.00 mm, 12.01 mm, 12.02 mm . . . 14.28 mm, 14.29 mm, 14.30 mm) and any value or range therebetween.

The plate 100 also has a maximum thickness 184 defined as the largest of a distance from the first surface 112 of the first portion 110 to the second surface 114 of the first portion 110, a distance from the first surface 112' of the second portion 110' to the second surface 114' of the second portion 110', or a distance from the first surface 162 of the bridge 160 to the second surface 164 of the bridge 160. The thickness of the first portion 110, the second portion 110', and the bridge 160 of the plate 100 shown in FIGS. 1A and 1B are all equal, but in other implementations, each of the first portion, the second portion, and the bridge can be different thicknesses. The thickness of each of the first portion 110, the second portion 110', and bridge 160 of the plate 100 shown in FIGS. 1A and 1B is 1.5 mm, and thus, the maximum thickness 184 of the plate 100 is 1.5 mm. However, in other implementations, the maximum thickness is 2 mm or less. Accordingly, the thickness 184 can be between about 1.5 mm and 2 mm (e.g., 1.50 mm, 1.51 mm, 1.52 mm . . . 1.98 mm, 1.99 mm, 2.00 mm) and any value or range therebetween.

Before the plate 100 is affixed to a spine 196, a physician must retract the tissue from the portion of the spine 196 to which the plate will be affixed. The retraction of tissue can lead to issues such as dysphagia, increased surgical time, and long recovery times. Thus, it is preferred that the plate 100 be as small as possible in all dimensions such that the necessary amount of retraction of tissue is kept to a minimum. The smaller dimensions of the plates 100 described herein, therefore, help to prevent complications in surgeries for fixating portions of a cervical spine to facilitate bone fusion.

Furthermore, the plates 100 described herein provide for a narrower bridge 160 than the plates of the prior art. Over time, osteophytes form and grow at the base of the vertebral bodies 198 of the spine 196. Before a plate 100 can be affixed to adjacent vertebral bodies 198, the osteophytes formed on the vertebral bodies 198 must be removed so that the plate 100 can be disposed on a relatively flat surface on the anterior surface of the cervical spine 196. This removal of osteophytes can lead to longer surgical times and longer recovery for the patient. Because the bridge 160 of the plates 100 described herein are narrower than those of existing plates, and the bridge 160 of the plate 100 spans the base of the vertebral body 198 where osteophytes form, less osteophyte removal is necessary to form a flat surface to which to affix the plate 100. Thus, the anterior cervical fixation plates 100 described herein provide for a plate 100 that can be implanted in less time with less future complications and a shorter average recovery time.

Figure 2A:
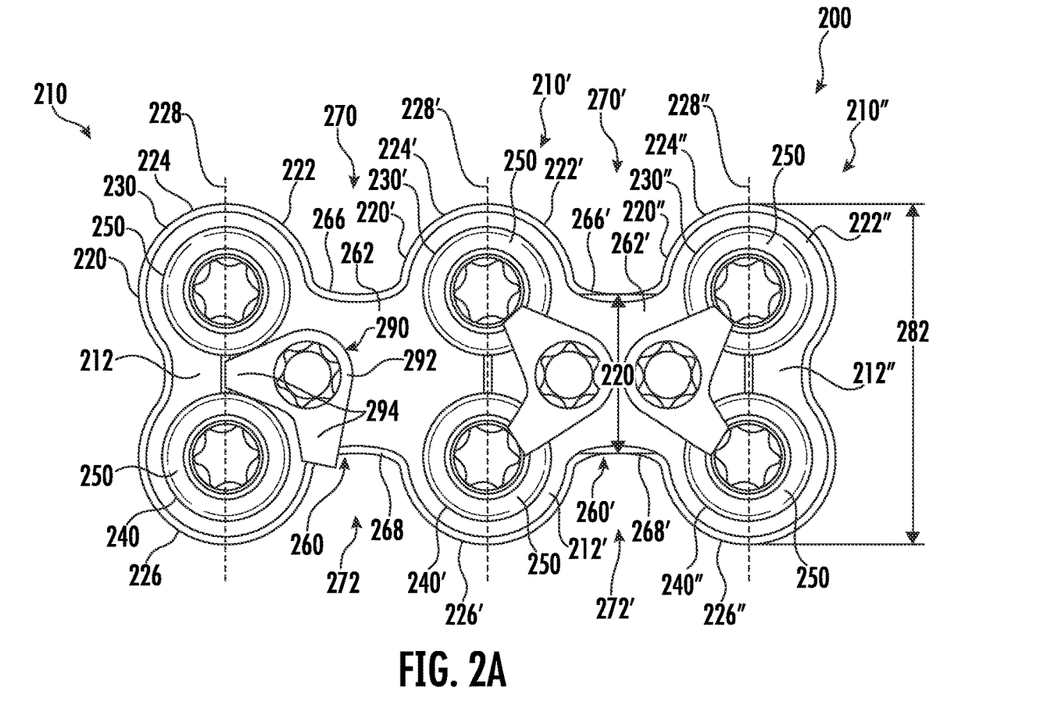
FIG. 2A is a top view of an anterior cervical fixation plate, according to another implementation.
Figure 2B:
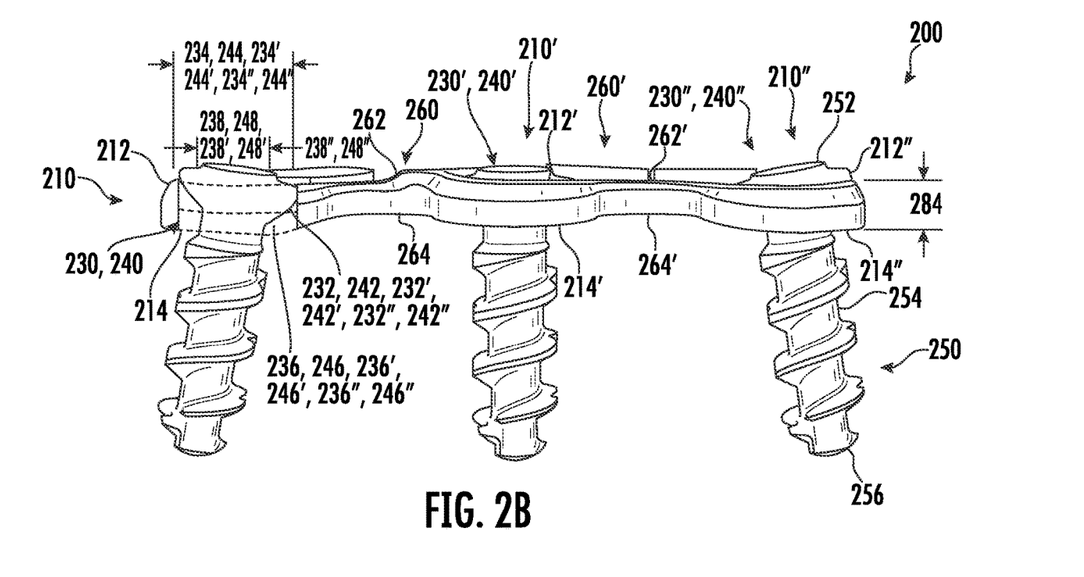
FIG. 2B is a side view of the anterior cervical fixation plate of FIG. 2A.

FIGS. 2A and 2B show another implementation of an anterior cervical fixation plate 200 for fixating portions of a cervical spine to facilitate bone fusion. The plate 200 shown in FIGS. 2A and 2B is similar to the plate 100 shown in FIGS. 1A and 1B, but the plate 200 shown in FIGS. 2A and 2B also includes a second bridge 260' and a third portion 210". This disclosure contemplates that the first portion 210 can attach at a first level (e.g., a first vertebral body), the second portion 210' can attach at a second level (e.g., a second vertebral body), and the third portion 210" can attach at a third level (e.g., a third vertebral body). Additionally, the bridge 160 connects the first and second portions 210, 210', and the second bridge 260' connects the second and third portions 210', 210". The plate 200 can accommodate six fasteners 250, e.g., two per level or two per vertebral body.

The third portion 210" of the plate 200 has a first surface 212" and a second surface 214" opposite and spaced apart from the third surface 212". The third portion 210" also has a first side 220", a second side 222" opposite and spaced apart from the first side 220" of the third portion 210", a third side 224", and a fourth side 226" opposite and spaced apart from the third side 224" of the third portion 210". The first 220", second 222", third 224", and fourth sides 226" extend between the first surface 212" and the second surface 214". The third portion 210" further includes a third axis 228" extending from the center of the third side 224" of the third portion 210" to the center of the fourth side 226" of the third portion 210".

The plate 200 includes a first bridge 260, similar to the bridge 160 included in the plate 100 shown in FIGS. 1A and 1B, and a second bridge 260'. The second bridge 260' has a first surface 262' and a second surface 264' opposite and spaced apart from the first surface 262' of the second bridge 260'. The second bridge 260' also has a first side 266' and a second side 268' opposite and spaced apart from the first side 266' of the second bridge 260'. The second bridge 260' is centrally located between the second portion 210' and the third portion 210", and the first side 266' and the second side 268' of the second bridge 260' each extend from the second side 222' of the second portion 210' to the first side 220" of the third portion 210".

A portion of the second side 222' of the second portion 210', a portion of the first side 220" of the third portion 210", and the first side 266' of the second bridge 260' define a third window 270', and a portion of the second side 222' of the second portion 210', a portion of the first side 220" of the third portion 210", and the second side 268' of the second bridge 260' define a fourth window 272'.

The first surface 212" of the third portion 210" defines a fifth fastener opening 230" and a sixth fastener opening 240". Each of the fifth fastener opening 230" and the sixth fastener opening 240" are aligned along the third axis 228" such that third axis 228" passes through at least a portion of the fastener openings 230", 240". Each of the fifth fastener opening 230" and the sixth fastener opening 240" extend from the first surface 212" of the third portion 210" to the second surface 214" of the third portion 210". The fifth fastener opening 230" and the sixth fastener opening 240" each have a first section 232", 242" with a first diameter 234", 244" and a second section 236", 246" with a second diameter 238", 248" that is smaller than the first diameter 234", 244". The first section 232", 242" of each fastener opening 230", 240" is closer than the second section 236", 246" to the first surface 212" of the third portion 210". Because the first diameters 234", 244" are larger than the second diameters 238", 248", the intersection of the first section 232", 242" and the second section 236", 246" of each fastener opening 230", 240" forms a lip 239", 349".

Although FIGS. 1A and 1B show a plate 100 including two portions 110, 110' and one bridge 160, and FIGS. 2A and 2B show a plate 200 including three portions 210, 210', 210" and two bridges 260, 260', in other implementations, a plate has any number of portions with bridges extending between each set of adjacent portions.

Figure 3:
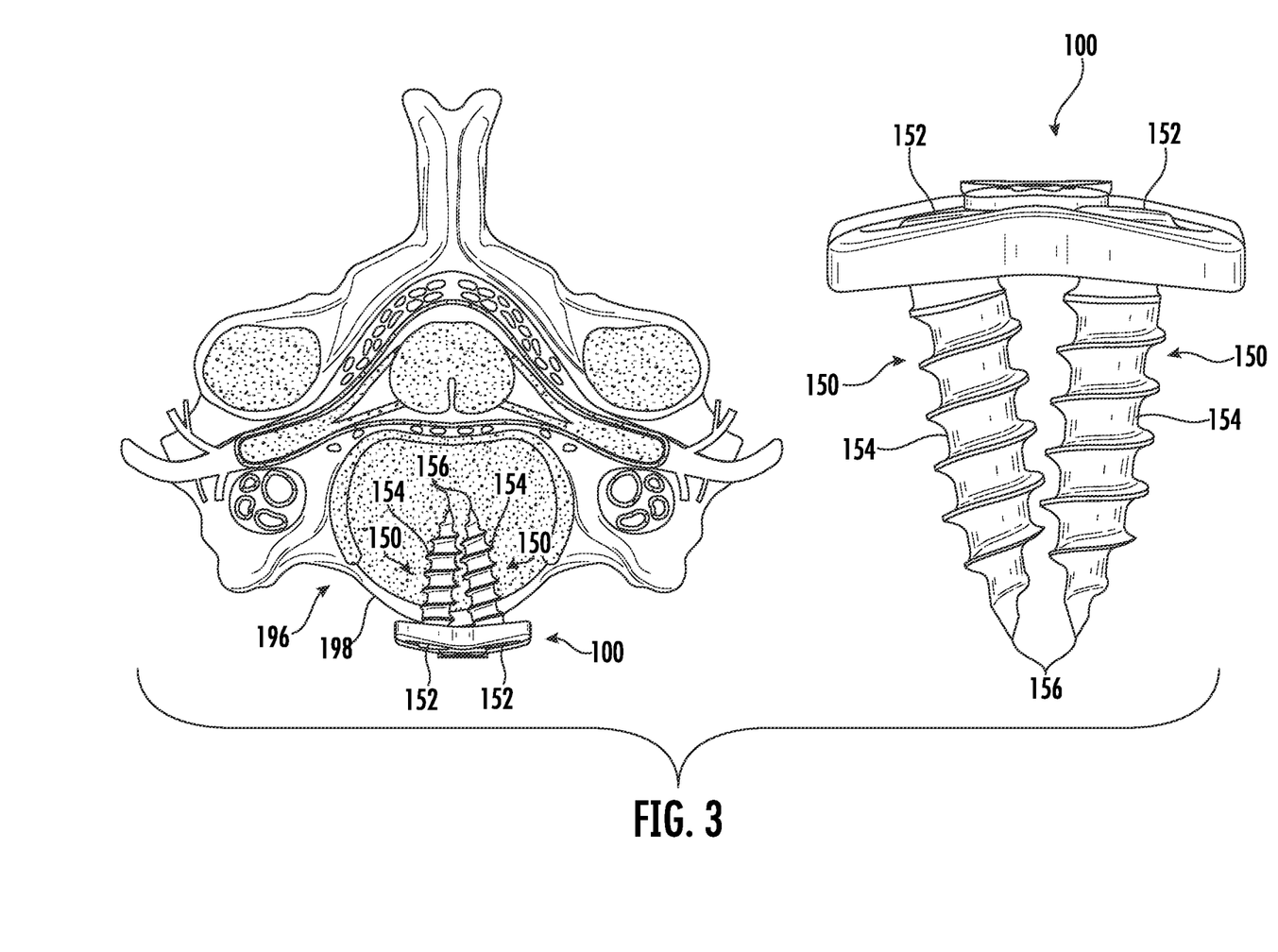
FIG. 3 is a perspective view of the anterior cervical fixation plate of FIGS. 1A and 1B affixed to a spine with the fasteners in a converging orientation.
Figure 4:
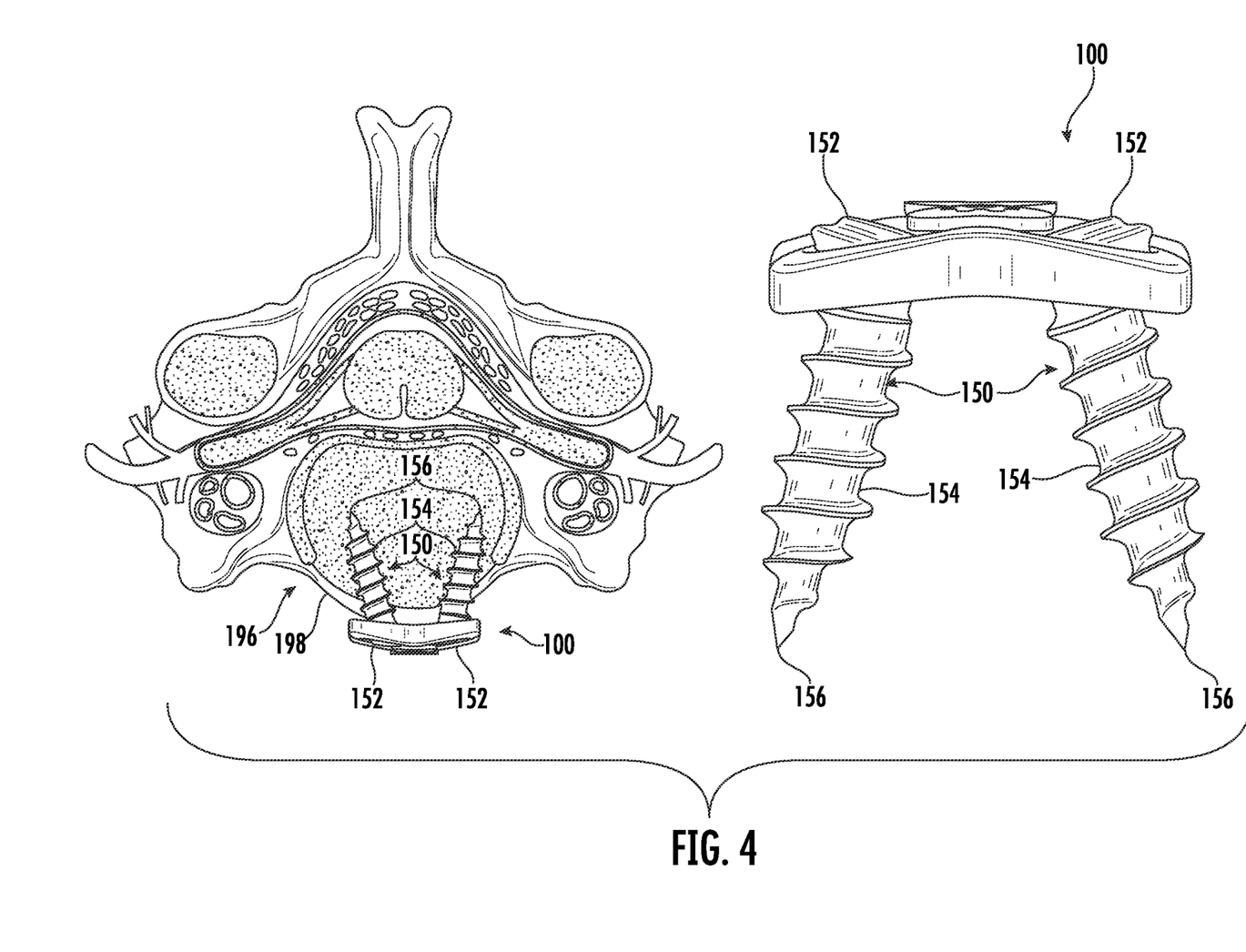
FIG. 4 is a perspective view of the anterior cervical fixation plate of FIGS. 1A and 1B affixed to a spine with the fasteners in a diverging orientation.

FIG. 3 shows the plate 100 of FIG. 1 affixed to a spine 196. As seen in FIG. 3, the fasteners 150 are in a converging orientation such that the tips 156 of the fasteners 150 are closer to each other than the heads 152 of the fasteners 150 are to each other. FIG. 4 also shows the plate 100 of FIG. 1 affixed to a spine 196. However, in FIG. 4, the fasteners 150 are in a diverging orientation such that the tips 156 of the fasteners 150 are further from each other than the heads 152 of the fasteners 150 are to each other.

It has been shown that when the fasteners 150 in an anterior cervical fixation plate 100 are in a diverging orientation, the fasteners 150 are less likely to pull out of the spine 196 than if the same fasteners 150 were oriented in the same plate 100 in the converging orientation. However, the width of many of the existing anterior cervical fixation plates cause the fastener openings in the plates to be too far apart from each other, which causes the heads of the fasteners to be too far from each other. Because the heads of the fasteners are so far apart from each other in many existing plates, the physician installing the plate on the spine of a patient risks the tips of the fasteners puncturing an artery, a vein, or a nerve if the plate is installed with the fasteners in the diverging orientation. Thus, many of the fastener openings of existing anterior cervical fixation plates are structured to prevent the fasteners from being oriented in a diverging orientation. However, as seen in FIG. 4, the plate width 182 of the anterior cervical fixation plates 100 described herein are narrow enough such that there is no risk of the tips 156 of the fasteners 150 puncturing an artery, a vein, or a nerve. The fastener openings 130, 140, 130', 140' of the plates 100 disclosed herein are designed with large enough first diameters 134, 144, 134', 144' and second diameters 138, 148, 138', 148' such that the fasteners 150 affixing the plate 100 to the spine 198 of a patient can be oriented in either the converging orientation or the diverging orientation.

Figure 5A:
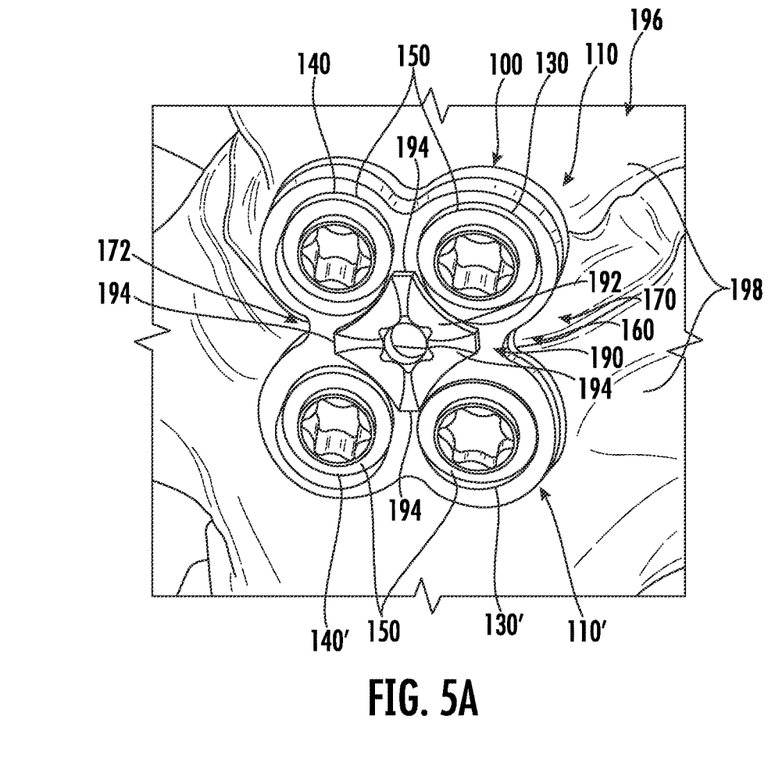
FIG. 5A is a perspective view of the anterior cervical fixation plate of FIGS. 1A and 1B with an anti-backout device in the first position.
Figure 5B:
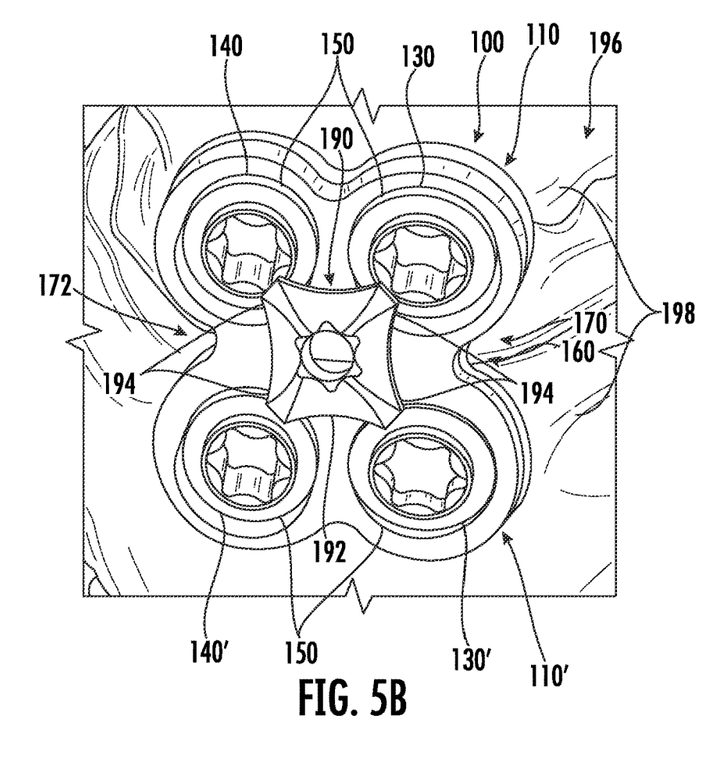
FIG. 5B is a perspective view of the anterior cervical fixation plate of FIGS. 1A and 1B with the anti-backout device in the second position.

FIGS. 5A and 5B show a detailed view of the anterior cervical fixation plate 100 of FIGS. 1A and 1B including an anti-backout device 190. The anti-backout device 190 has a body 192 and four locking tabs 194 extending radially from the body 192. The body 192 is rotatably coupled to the first surface 162 of the bridge 160, and the anti-backout device 190 is rotatable relative to the bridge 160 from a first position (shown in FIG. 5A) to a second position (shown in FIG. 5B). The locking tabs 194 are structured such that, when the anti-backout device 190 is in the first position, none of the four locking tabs 194 are covering any portion of the first 130, second 140, third 130', or fourth fastener openings 140'. After the anti-backout device 190 has been rotated from the first position to the second position, each of the four locking tabs 194 is at least partially covering one of the four fastener openings 130, 140, 130', 140' such that the locking tabs 194 are in a position to prevent the fasteners 150 disposed in each of the four fastener openings 130, 140, 130', 140' from coming out of the fastener's 150 respective fastener opening 130, 140, 130', 140' (also called "backing out"). When a plate 100 is affixed to a spine 196 by driving fasteners 150 through each of the fastener openings 130, 140, 130', 140' and into the vertebrae 198 of the patient, the anti-backout device 190 can be rotated to the second position to prevent the fasteners 150 from backing out of the spine 196.

FIGS. 2A and 2B shows an implementation of an anti-backout device 290 including only two locking tabs 294 extending from the body 292. Thus, the anti-backout devices 290 shown in FIGS. 2A and 2B are each used for preventing the fasteners 250 disposed in only two fastener openings from backing out. Because there are six total fastener openings 230, 240, 230', 240', 230", 240" in the plate 200 shown in FIGS. 2A and 2B, the plate 200 includes three anti-backout devices 290. However, in other implementations, a plate can include any number of anti-backout devices having any number of locking tabs for covering any number of fastener openings defined by the plate. In some implementations, the plate includes one anti-backout device for each fastener opening defined by the plate, and each anti-backout device has only one locking tab for covering one fastener opening. In some implementations, a locking tab of the anti-backout device covers two or more fastener openings in the second position.

This disclosure contemplates that the devices described herein can be made using alternative medical grade materials. In some implementations, the device can be made of a molybdenum-rhenium (MoRe) alloy. Optionally, the MoRe alloy is Mo47.5Re. Alternatively, the alloy is optionally 99.99% pure with at least 40 weight percent (wt %) rhenium. Optionally, the alloy is optionally 99.99% pure with between 40 wt % and 99.9 wt % rhenium (e.g., 40.0 wt %, 40.01 wt %, 40.02 wt % . . . 99.88 wt %, 99.89 wt %, 99.9 wt %) and any value or range therebetween. In other implementations, the device can be made of titanium (Ti). In other implementations, the device can be made of a titanium-molybdenum (TiMo) alloy including, but not limited to, Ti-15Mo. In other implementations, the device can be made of a titanium (Ti) alloy. In other implementations, the device can be made of a cobalt-chromium (CoCr) alloy. Other example alloys that can be used are described, for example, in U.S. 2019/0008995, published Jan. 10, 2019, titled "Molybdenum Alloys for Medical Devices," the disclosure of which is expressly incorporated herein by reference in its entirety.

A number of implementations have been described. Nevertheless, it will be understood that various modifications may be made without departing from the spirit and scope of the claims. Accordingly, other implementations are within the scope of the following claims.

Certain terminology is used herein for convenience only and is not to be taken as a limitation on the present claims. In the drawings, the same reference numbers are employed for designating the same elements throughout the several figures. A number of examples are provided, nevertheless, it will be understood that various modifications can be made without departing from the spirit and scope of the disclosure herein. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. Although the terms "comprising" and "including" have been used herein to describe various implementations, the terms "consisting essentially of" and "consisting of" can be used in place of "comprising" and "including" to provide for more specific implementations and are also disclosed.

What is claimed is:

1. An anterior cervical fixation plate for fixating portions of a cervical spine to facilitate bone fusion; said anterior cervical fixation plate comprising:

a first portion having a first surface, a second surface opposite and spaced apart from said first surface of said first portion, a first side, a second side opposite and spaced apart from said first side of said first portion, a third side, a fourth side opposite and spaced apart from said third side of said first portion, and a first axis extending from said third side of said first portion to said fourth side of said first portion; said first surface of said first portion includes a first fastener opening and a second fastener opening; each of said first fastener opening and said second fastener opening is aligned along said first axis; each of said first fastener opening and said second fastener opening extends from said first surface of said first portion to said second surface of said first portion;

a second portion having a first surface, a second surface opposite and spaced apart from said first surface of said second portion, a first side, a second side opposite and spaced apart from said first side of said second portion, a third side, a fourth side opposite and spaced apart from said third side of said second portion, and a second axis extending from said third side of said second portion to said fourth side of said second portion; said first surface of said second portion includes a third fastener opening and a fourth fastener opening; each of said third fastener opening and said fourth fastener opening is aligned along said second axis; each of said third fastener opening and said fourth fastener opening extends from said first surface of said second portion to said second surface of said second portion; and a bridge having a first surface, a second surface opposite and spaced apart from said first surface of said bridge, a first side, and a second side opposite and spaced apart from said first side of said bridge; said bridge is located between said first portion and said second portion; said first side and said second side of said bridge each extends from said second side of said first portion to said first side of said second portion; said second side of said first portion, said first side of said second portion, and said first side of said bridge define a first window; said second side of said first portion, said first side of said second portion, and said second side of said bridge define a second window; a distance between said first and second windows is less than a distance between said first side of said first portion and said second side of said second portion; said first side of bridge forms a base of said first window; said base of said first window defining a narrowest portion of said first window and a width of said first window increases as a distance increases outwardly from said base of said first window; said second side of bridge forms a base of said second window; said base of said second window defining a narrowest portion of said second window and a width of said second window increases as a distance increases outwardly from said base of said second window.

2. The anterior cervical fixation plate as defined in claim 1, wherein said a distance between said first and second windows is no more than 4.3 mm;

said bridge is centrally located between said first portion and said second portion.

3. The anterior cervical fixation plate as defined in claim 1, wherein at least one of said first, second, third, and fourth fastener openings is in a diverging orientation relative to a central axis of said anterior cervical fixation plate when said anterior cervical fixation plate is affixed to portions of a cervical spine.

4. The anterior cervical fixation plate as defined in claim 1, wherein each of said first, second, third, and fourth fastener openings has a first section that has a first diameter and a second section that has a second diameter; said first section is closer than said second section to a respective first surface of said first or second portion;

said first diameter is greater than said second diameter.

5. The anterior cervical fixation plate as defined in claim 4, wherein said first diameter and said second diameter of each of said first, second, third, and fourth fastener openings allows for disposing of a fastener through each of said fastener openings such that said fastener is in a converging orientation when said plate is affixed to portions of a cervical spine.

6. The anterior cervical fixation plate as defined in claim 1, wherein said anterior cervical fixation plate has a plate thickness that is defined as a largest of a) a distance from said first surface of said first portion to said second surface of said first portion, b) a distance from said first surface of said second portion to said second surface of said second portion, or c) a distance from said first surface of said bridge to said second surface of said bridge; said plate thickness is no more than 2 mm.

7. The anterior cervical fixation plate as defined in claim 1, wherein said anterior cervical fixation plate has a plate width that is defined as a largest of a) a distance from said third side of said first portion to said fourth side of said first portion, or b) a distance from said third side of said second portion to said fourth side of said second portion; said plate width is no more than 14.3 mm.

8. The anterior cervical fixation plate as defined in claim 1, further including an anti-backout device that is configured to be coupled to said first surface of said bridge; said anti-backout device is configured to be movable from a first position to a second position; said anti-backout device is configured to not overlie said first, second third and fourth fastener openings in said first position; said anti-backout device is configured to at least partially overlie said first, second third and fourth fastener openings in said second position.

9. The anterior cervical fixation plate as defined in claim 1, wherein said anterior cervical fixation plate is at least partially formed of one or more materials a) molybdenum-rhenium (MoRe) alloy, b) titanium-molybdenum (TiMo) alloy, c) cobalt-chromium (CoCr) alloy, and/or d) titanium (Ti) alloy.

10. An anterior cervical fixation plate for fixating portions of a cervical spine to facilitate bone fusion; said anterior cervical fixation plate comprising:
- a first portion having a first surface, a second surface opposite and spaced apart from said first surface of said first portion, a first side, a second side opposite and spaced apart from said first side of said first portion, a third side, a fourth side opposite and spaced apart from said third side of said first portion, and a first axis extending from said third side of said first portion to said fourth side of said first portion; said first surface of said first portion includes a first fastener opening and a second fastener opening; each of said first fastener opening and said second fastener opening is aligned along said first axis; each of said first fastener opening and said second fastener opening extends from said first surface of said first portion to said second surface of said first portion;
- a second portion having a first surface, a second surface opposite and spaced apart from said first surface of said second portion, a first side, a second side opposite and spaced apart from said first side of said second portion, a third side, a fourth side opposite and spaced apart from said third side of said second portion, and a second axis extending from said third side of said second portion to said fourth side of said second portion; said first surface of said second portion includes a third fastener opening and a fourth fastener opening; each of said third fastener opening and said fourth fastener opening is aligned along said second axis; each of said third fastener opening and said fourth fastener opening extends from said first surface of said second portion to said second surface of said second portion;
- a bridge having a first surface, a second surface opposite and spaced apart from said first surface of said bridge, a first side, and a second side opposite and spaced apart from said first side of said bridge; said bridge is located between said first portion and said second portion; said first side and said second side of said bridge each extends from said second side of said first portion to said first side of said second portion; said second side of said first portion, said first side of said second portion, and said first side of said bridge define a first window; said second side of said first portion, said first side of said second portion, and said second side of said bridge define a second window; a distance between said first and second windows is less than a distance between said first side of said first portion and said second side of said second portion; said first side of bridge forms a base of said first window; said base of said first window defining a narrowest portion of said first window and a width of said first window increases as a distance increases outwardly from said base of said first window; said second side of bridge forms a base of said second window; said base of said second window defining a narrowest portion of said second window and a width of said second window increases as a distance increases outwardly from said base of said second window; and
- an anti-backout device that is configured to be coupled to said first surface of said bridge;
- said anti-backout device is configured to be movable from a first position to a second position; said anti-backout device is configured to not overlie said first, second third and fourth fastener openings in said first position; said anti-backout device is configured to at least partially overlie said first, second third and fourth fastener openings in said second position; and
- wherein two or more of said first, second, third, and fourth fastener openings is in a diverging orientation relative to a central axis of said anterior cervical fixation plate when said anterior cervical fixation plate is affixed to portions of a cervical spine.

* * * * *